United States Patent [19]

Kobayashi et al.

[11] Patent Number: 5,489,469
[45] Date of Patent: Feb. 6, 1996

[54] ABSORBENT COMPOSITE

[75] Inventors: Takatoshi Kobayashi, Utsunomiya; Yukihiro Nakano; Zenbei Meiwa, both of Wakayama; Minoru Nakanishi, Utsunomiya; Tadashi Matsui, Wakayama, all of Japan

[73] Assignee: Kao Corporation, Tokyo, Japan

[21] Appl. No.: 68,288

[22] Filed: May 28, 1993

Related U.S. Application Data

[63] Continuation of Ser. No. 782,725, Oct. 28, 1991, abandoned, which is a continuation of Ser. No. 492,383, Mar. 9, 1990, abandoned, which is a continuation of Ser. No. 146,734, Jan. 21, 1988, abandoned.

[30] Foreign Application Priority Data

Jan. 28, 1987 [JP] Japan ................................. 62-17946
Apr. 1, 1987 [JP] Japan ................................. 62-80089
Apr. 24, 1987 [JP] Japan ................................. 62-101468

[51] Int. Cl.⁶ .................................................. B32B 5/16
[52] U.S. Cl. ........................ 428/283; 428/288; 428/270; 428/357; 428/359; 428/360; 428/361; 428/392; 428/393; 428/400; 604/365; 604/367; 604/368; 604/372; 604/374; 604/377
[58] Field of Search ..................... 428/393, 392, 428/372, 378, 379, 357, 359, 360, 361, 241, 375, 288, 290, 283, 403; 524/35, 15; 523/11; 604/367, 374, 377; 427/272, 212, 180, 201

[56] References Cited

U.S. PATENT DOCUMENTS

| | | | |
|---|---|---|---|
| 2,750,944 | 6/1956 | Tollstrup | 604/368 |
| 3,670,731 | 6/1972 | Harmon | 604/368 |
| 3,901,236 | 8/1975 | Assarsson et al. | 128/284 |
| 3,932,322 | 1/1976 | Duchane | 604/368 |
| 3,935,363 | 1/1976 | Burkholder et al. | 604/374 |
| 4,364,992 | 12/1982 | Ito et al. | 428/288 |
| 4,381,783 | 5/1983 | Elias | 604/375 |
| 4,415,388 | 11/1983 | Korpman | 156/78 |
| 4,429,001 | 1/1984 | Kolpin et al. | 428/283 |
| 4,500,670 | 2/1985 | McKinley et al. | 604/364 |
| 4,525,410 | 6/1985 | Hagiwara | 428/283 |
| 4,693,713 | 9/1987 | Chmelir et al. | 604/368 |
| 4,718,899 | 1/1988 | Itoh et al. | 523/111 |
| 4,721,647 | 1/1988 | Nakanishi | 428/288 |
| 4,748,076 | 5/1988 | Saotome | 428/361 |
| 5,002,814 | 3/1991 | Knack et al. | 428/402 |

FOREIGN PATENT DOCUMENTS

| | | |
|---|---|---|
| 0053928 | 6/1982 | European Pat. Off. . |
| 0122042 | 10/1984 | European Pat. Off. . |
| 55-71728 | 5/1980 | Japan . |
| 58-501107 | 7/1983 | Japan . |
| 59-8711 | 1/1984 | Japan . |
| 59-86657 | 5/1984 | Japan . |
| 2082614 | 3/1982 | United Kingdom . |
| 2162525 | 2/1986 | United Kingdom . |
| 8604910 | 8/1986 | WIPO . |

Primary Examiner—Patrick J. Ryan
Assistant Examiner—J. M. Gray
Attorney, Agent, or Firm—Birch, Stewart, Kolasch & Birch

[57] ABSTRACT

A liquid-absorbent composite comprises (a) a water-absorbent polymer, (b) a water-insoluble inorganic material and (c) a water-insoluble hydrophilic fibrous material at a weight ratio between (a), (b) and (c) in the range of 100:5–1200:5–1200. It is very useful as the absorbent component for a sanitary napkin and a medical pad.

8 Claims, 2 Drawing Sheets

FIG. 1(a)
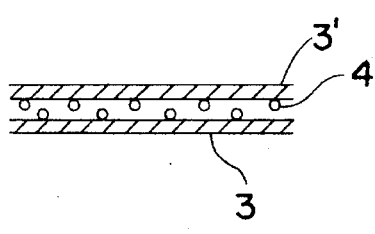
FIG. 1(b)
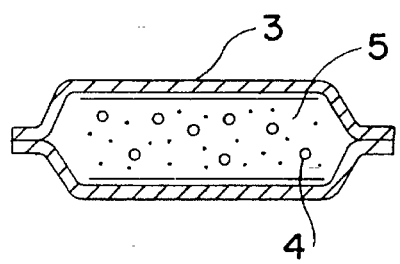
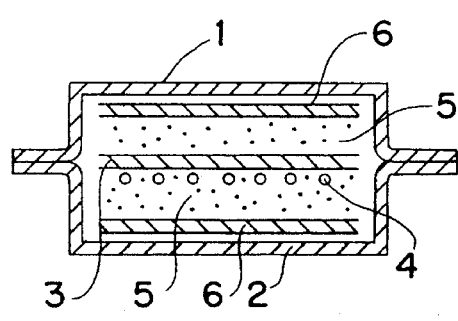
FIG. 1(c)
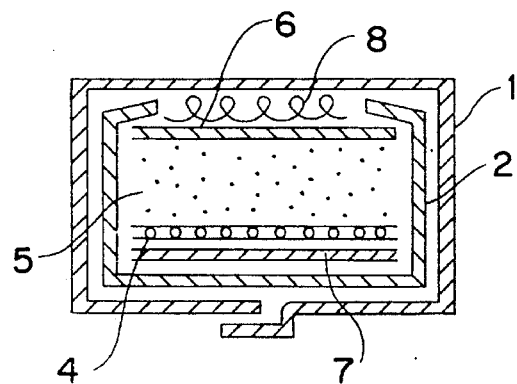
FIG. 1(d)

ABSORBENT COMPOSITE

This application is a continuation of application Ser. No. 07/782,725 filed on Oct. 28, 1991, now abandoned, which is a continuation of application Ser. No. 07/492,383 filed on Mar. 9, 1990, now abandoned, which was a continuation of application Ser. No. 07/146,734 filed Jan. 21, 1988, now abandoned.

FIELD OF INDUSTRIAL APPLICATION

The invention relates to an absorbent composite, a process for manufacturing the same and an absorbent article including the same. In particular, the absorbent composite is useful as an absorbent article such that the absorption of a liquid and the retention of the absorbed liquid are required, e.g., hygienic and medical supplies such as sanitary napkins and disposable diapers and a water retaining agent for the agricultural and forestry filed and a freshness retaining agent for vegetables. It may be used as a sanitary pad such as a mother's milk pad, a childbed pad, an incontinence pad, a haemorrhoids pad and a surgical pad.

STATEMENT OF PRIOR ARTS

In recent years, a polymer capable of absorbing water in an amount of several tens to several hundreds times its own weight, the so-called water absorbent polymer has been developed and is used in hygienic supplies such as sanitary napkins and paper diapers, medical materials such as a contact lenses and coatings of sutures, separation and purification materials such as carriers for liquid chromatography, or water retaining or water absorbing materials in the fields of agriculture and forestry and the civil engineering industries.

Examples of known water absorbent polymers of the kind as mentioned above include crosslinked polyacrylates, starch-acrylic acid graft copolymers, hydrolyzates of cellulose-acrylonitrile graft polymers, and hydrolyzates of vinyl acetate-acrylate copolymers. These water absorbent polymers exhibit excellent absorbency with respect to low-viscosity liquids such as water and urine and can rapidly absorb them in large amounts. Further, various proposals on the improvement thereof have been made.

On the other hand, proposals with respect to a water absorbent polymer for absorption of a high-viscosity liquid, such as blood, include conversion thereof into a porous water absorbent polymer (see Japanese Patent Laid-Open Nos. 71728/80 and 8711/84), addition of water-soluble organic and/or inorganic salts (see Published Japanese Translation of PCT Patent Application No. 501107/1983), and mixing with a hydrophilic fiber such as pulp (see Japanese Patent Laid-Open No. 86657/1984). However, the effects attained by these methods are not satisfactory.

Therefore, it is desired to develop a water absorbent polymer which is excellent in absorbency, i.e., excellent in capacity, rate and power of absorbing not only with respect to a low-viscosity liquid but also with respect to a high-viscosity liquid.

SUMMARY OF THE INVENTION

Under the above-mentioned circumstances, the present inventors made extensive and intensive studies with a view to developing an absorber which is excellent in capacity, rate and power of absorbing not only with respect to low-viscosity liquids such as water, urine and serous bodily fluid but also with respect to high-viscosity liquids such as blood, bodily fluids and loose passages. As a result, the present inventors have found that a composite having unprecedentedly excellent absorbency can be obtained by adding and immobilizing given amounts of a water-insoluble inorganic material and a water-insoluble hydrophilic fibrous material to a water absorbent polymer, which led to the completion of the present invention.

A liquid-absorbent composite of the invention comprises (a) a water-absorbent polymer, (b) a water-insoluble inorganic material and (c) a water-insoluble hydrophilic fibrous material at a weight ratio between (a), (b) and (c) in the range of 100:5–1200:5–1200.

It is preferable that it has a bulk specific gravity of 0.03 to 0.7 g/cc. The polymer may be one formed from a water-soluble, ethylenically unsaturated monomer or a crosslinked product thereof, including acrylic acid or a salt of acrylic acid as the major component. The inorganic material (b) is selected from the group consisting of alumina, silica, zeolite, a clay of the montmorillonite group and a clay of the kaolinite group. The fibrous material (c) is cellulose, natural or artificial.

The invention provides an absorbent article comprising the absorbent composite as defined above.

The invention also provides a process for manufacturing the absorbent composite as defined above by mixing (a), (b) and (c) with one another in the presence of 70 to 3000 parts by weight, based on 100 parts by weight of (a), of water. The process may further comprise the step of drying the mixture.

The water absorbent polymer useful for the present invention is generally any polymer having water absorbency. Examples of such a polymer include a polyacrylate and a crosslinking product thereof, polyethylene oxide, polyvinyl pyrrolidone, crosslinked sulfonated polystyrene and polyvinylpyridine, a saponified starch-poly(meth)acrylonitrile graft copolymer, a starch-poly(meth)acrylic acid (and its salt) graft copolymer (and its crosslinking product), a product obtained by a reaction of polyvinyl alcohol with maleic anhydride (and its salt), and a hydrolyzate of a starch-poly(meth)acrylate graft copolymer. Further, polyvinyl alcohol sulfonate, a polyvinyl alcohol-acrylic acid graft copolymer, etc. may also be employed. A preferable polymer is a polymer of a water-soluble ethylenically unsaturated monomer composed mainly Of acrylic acid or an acrylate, or a crosslinking product of said polymer, wherein the polymer may be produced by any method.

These polymers may be used in any combination of two or more. The water absorbent polymer is a polymer capable of absorbing water in an amount of 20 cc/g of the polymer and is in the form of powder, granule, mass, and sheet. The composite of the present invention can be produced from a polymer in any of the above-mentioned forms. When the polymer is used in a powdery or granular form, it is preferred that the particle diameter be 10 to 3000 μm, preferably 15 to 1000 μm.

The inorganic material to be used in the present invention should be substantially insoluble in water, and any material meeting this essential requirement may be used. Examples of the inorganic material used in the present invention include alumina, silica, titanium dioxide, talc, zirconia, calcium phosphate, barium phosphate, calcium sulfate, clay, silicic acid, diatomaceous earth, bentonite, activated carbon, zeolite, kaolin, acid clay, activated clay, vermiculite, and other metal oxides. Alumina, silica, zeolite, montmorillonite group clay (bentonite), and kaolinite group clay (kaolin) are particularly preferable. The particle diameter of the water-insoluble inorganic material is not particularly limited. However, the particle diameter is preferably 1500 μm or less, particularly preferably 500 μm or less.

Examples of the water-insoluble hydrophilic fibrous material useful for the present invention incude materials having wettability and liquid guiding properties characteristic of water-insoluble fibrous materials, such as cellulose powder, pulp, rayon, vinylon, cotton, wool, and cellulose acetate. The use of cellulose powder of natural cellulose or artificial cellulose, pulp, and rayon is particularly preferable. Further, in order to impart functions such as immobilization through fusion, hydrophobic fibrous materials, such as polyester, polyethylene, polypropylene, polyvinyl chloride, acrylics, and nylon, can be also used in the form of a mixture with these water-insoluble hydrophilic fibrous materials. Although the hydrophobic fibrous material may be used in a wide range of mixing ratios according to the applications of the composite so long as the hydrophilic nature is not spoiled, it is preferred that the content of the water-insoluble hydrophilic fibrous material be 60% by weight or more, preferably 80% by weight or more. The fibrous material may be used in any form of long fiber, short fiber and fine powder. The fiber length is preferably 50 mm or less, more preferably 40 mm or less.

The water absorbent polymer, water-insoluble inorganic material, and water-insoluble hydrophilic fibrous material are used in such a composite ratio that the amounts of the water-insoluble inorganic material and water-insoluble hydrophilic fibrous material each based on 100 parts by weight of the water absorbent polymer are 5 to 1200 parts by weight and 5 to 1200 parts by weight, respectively, preferably 10 to 800 parts by weight and 10 to 1000 parts by weight, respectively, more preferably 20 to 500 parts by weight and 20 to 800 parts by weight, respectively. The absence of any of these constituents does not bring about the effect of the present invention and, therefore, is contrary to the intention of the present invention. When the content of the water-insoluble inorganic material is less than 5 parts by weight, the rate of absorption and absorbing power of the liquid absorbent composite are unfavorably small. On the other hand, when the content exceeds 1200 parts by weight, not only is the capacity of absorption of the composite lowered, but also the water-insoluble inorganic material is not immobilized on the polymer, which makes it impossible to attain the purposes of the present invention. When the content of the water-insoluble hydrophilic fibrous material is less than 5 parts by weight, the effects on liquid guiding properties and rate of absorption of the liquid absorbent composite are small, while when the content exceeds 1200 parts by weight, the capacity of absorption of the liquid absorbent composite is small, which makes it impossible to attain the purpose of the present invention. The composite ratio of the water-insoluble inorganic material to the water-insoluble hydrophilic fibrous material may be varied at will in the above-mentioned range according to the kind of the liquid to be absorbed and applications.

Although known methods may be employed to prepare the liquid absorbent composite according to the present invention, the following method is preferable.

Specifically, the liquid absorbent composite is prepared, by adding a water-insoluble inorganic material and a water-insoluble hydrophilic fibrous material to a water absorbent polymer which is in a sufficiently swelled state. Example of the method include a method which comprises feeding a swelled polymer, a water-insoluble inorganic material, and a water-insoluble hydrophilic fibrous material into a kneader-mixer, mixing them with each other and drying the resulting product, a method which comprises successively adding a water absorbent polymer, water, a water-insoluble inorganic material and a water-insoluble hydrophilic fibrous material to an organic solvent while stirring, subjecting the resulting mixture to filtration and drying the filter cake, and a method which comprises mixing a water-insoluble inorganic material with water in a screw rotary vane mixer, successively adding a water absorbent polymer and a water-insoluble hydrophilic fibrous material to the resulting mixture, mixing them with each other, and drying the resulting product. Other methods including a method which comprises adding a water-insoluble inorganic material and a water-insoluble hydrophilic fibrous material to a water-soluble ethylenically unsaturated monomer or a water-soluble ethylenically unsaturated monomer containing a crosslinking agent, allowing the monomer to polymerize, and drying the resulting product may be also employed, and the method of preparing a liquid absorbent composite is not limited to these ones. If necessary, the liquid absorbent composite as dried may be subjected to a treatment-such as pulverization.

In addition, the invention provides a new process for manufacturing the absorbent composite effectively. It comprises adding water to a water absorbent polymer which can absorb water in an amount of about 20 cc or more per one gram of the polymer, then adding a water-insoluble inorganic material and a water-insoluble hydrophilic fibrous material to the water absorbent polymer which is in a swelled state and mixing them with each other, thereby depositing or bonding the water-insoluble inorganic material and water-insoluble hydrophilic fibrous material to the swelled water absorbent polymer and, if necessary, drying the resulting product.

Water may be added not only in the form of a liquid but also by spraying or blowing in the form of steam, and any of these methods can be favorably employed.

The order and method of feeding the water absorbent polymer, water-insoluble inorganic material, water-insoluble hydrophilic fibrous material, and water are not particularly limited. However, a method in which the water-insoluble inorganic material and water-insoluble hydrophilic fibrous material are together added to the swelled polymer and a method in which the water-insoluble hydrophilic fibrous material is added to a mixture obtained by kneading the water absorbent polymer, water, and water insoluble inorganic material are preferably employed, because in these methods the functions of each material are sufficiently manifested.

The method of mixing the above-mentioned individual materials is not also particularly limited and includes a method which comprises feeding a swelled polymer, a water-insoluble inorganic material, and a water-insoluble hydrophilic fibrous material into a mixer of a rotating container type or a mixer of the stationary container type, mixing them with each other and drying the resulting product, a method which comprises mixing a water-insoluble inorganic material with water, successively adding a water absorbent polymer and a water-insoluble hydrophilic fibrous material to the resulting mixture, mixing them each other and drying the resulting product, and a method which comprises successively adding a water absorbent polymer, water, a water-insoluble inorganic material and a water-insoluble hydrophilic fibrous material to an organic solvent substantially incompatible with water while stirring, subjecting the resulting mixture to filtration and drying the filter cake.

In converting the above-mentioned water absorbent polymer, water-insoluble inorganic material and water-insoluble hydrophilic fibrous material into a composite through the medium of water, water is required to be present in an amount of 70 to 3000 parts by weight, preferably 200 to 1500 parts by weight based on 100 parts by weight of the water absorbent polymer. When the amount of water is less than 70 parts by weight, the deposition or bonding of the water-insoluble inorganic material and water-insoluble hydrophilic fibrous material to the water absorbent polymer is insufficient, which unfaborably makes it impossible to satisfactorily exhibit an effect attained by conversion to a composite. On the other hand, when the amount of water exceeds 3000 parts by weight, the gel strength of the water absorbent polymer is excessively lowered, which makes it difficult to conduct the conversion to a composite while maintaining the form of a polymer, thus causing a great change in the form of the resulting composite. This brings about not only a lowering in performance but also an increase in drying time and cost of drying.

When the water absorbent polymer is used in a dried form, water may be added in an amount as mentioned above in the above-mentioned method. Alternatively, the water absorbent polymer used may originally contain water in an amount corresponding to a part or the whole of the above-mentioned amount. That is, a water-containing polymer before drying in the process for preparing a water absorbent polymer may be used as it is for production of a liquid absorbent composite according to the present invention.

If necessary, the liquid absorbent composite is dried after mixing. The method of drying is not particularly limited, and the composite can be dried by a suitable method, e.g., under atmospheric or reduced pressure at room temperature or with heating while allowing it to stand or stirring.

The water content of the liquid absorbent composite after drying is preferably 50% by weight or less, more preferably 30 wt. % or less, particularly preferably 20 wt. % or less from the standpoint of handleability and absorbency of the product.

The liquid absorbent composite of the present invention thus prepared has a bulk specific gravity of 0.03 to 0.7 g/cc, preferably 0.05 to 0.6 g/cc.

A water absorbent polymer (A), a water-insoluble inorganic material (B) and a water-insoluble hydrophilic fibrous material (C) are in the following conditions when they constitute the liquid absorbent composite of the invention. That is, the water-insoluble hydrophilic fibrous material and the water-insoluble inorganic material form a composite in cooperation with the water absorbent polymer in the following states.

Water-Insoluble Hydrophilic Fibrous Material

① The fiber is partly or entirely embedded in the polymer.

② The fiber is deposited on the surface of the polymer.

③ The fibers are entwined with one another and party embedded in the polymer or deposited on the surface of the polymer.

④ The polymer and the fiber are bonded to each other through the medium of the inorganic material.

Water-Insoluble Inorganic Material

① The inorganic material is partly or entirely embedded in the polymer.

② The inorganic material is deposited on the surface of the polymer.

③ The inorganic material is deposited on the fiber which is in the state as mentioned with respect to <fibrous material> in the above items ① to ④.

④ The inorganic materials are agglomerated and partly embedded in the polymer or deposited on the surface of the polymer.

Examples of the states of a water absorbent polymer (A), a water-insoluble inorganic material (B), and a water-insoluble hydrophilic fibrous material (C) when they constitute the liquid absorbent composite include the above-mentioned ones. However, the present invention is not limited to these examples, and it will suffice in the present invention when the components (A), (B), and (C) are practically combined.

The improvement in liquid absorbency by virtue of the water-insoluble inorganic material and the water-insoluble hydrophilic fibrous material contained in the liquid absorbent composite of the present invention is remarkable particularly with respect to high-viscosity liquids. It is believed that this function was exhibited as follows.

The water absorbent polymer is coated with the water-insoluble hydrophilic fibrous material, which not only improves the adaptability to an aqueous solution but also enables the polymer to be swelled even when the liquid is not directly contacted with the polymer as far as the liquid is contacted with the water-insoluble hydrophilic fibrous material with which the water absorbent polymer is coated because the liquid is sent to the polymer through the liquid guiding effect of the fiber.

It is preferred that the inorganic material used in the present invention be substantially insoluble in water and hygroscopic to a certain extent. The inorganic material is partly included in the polymer. The water absorbent polymer having a smooth surface is covered with a dense coating of the finely divided inorganic material, which causes capillary action in the spaces between the inorganic material particles, thus leading to enhancement of the absorbency of the water absorbent polymer. Therefore, the combination of both the water-insoluble inorganic material and the water-insoluble hydrophilic fibrous material with the water absorbent polymer leads to an improvement in performance, i.e., the attainment of the purpose of the present invention.

BRIEF DESCRIPTION OF THE DRAWINGS

FIG. 1 is a cross-sectional view of various embodiments of the absorbent articles of the present invention.

Figure 2:
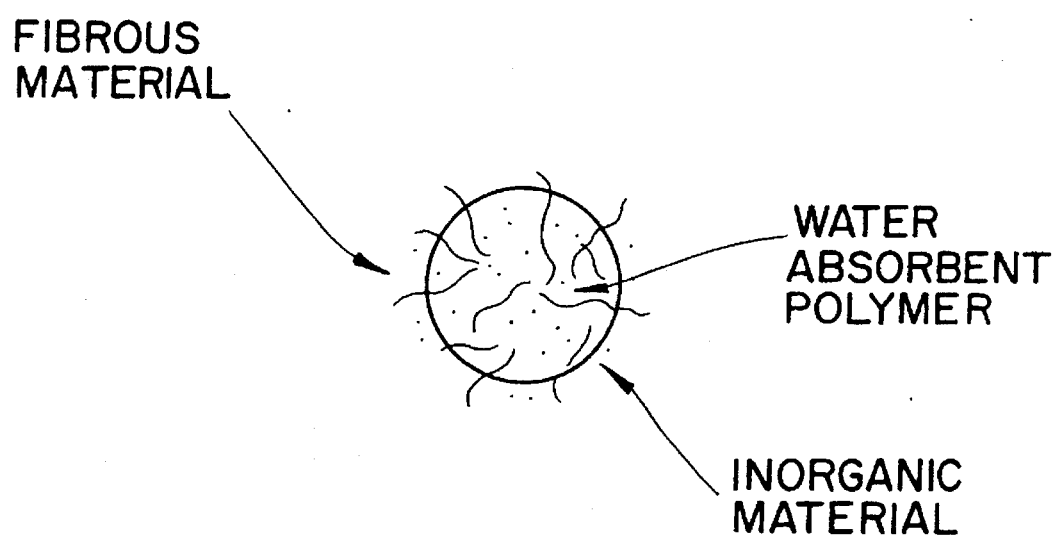
FIG. 2 is a schematic view of the liquid absorbent composite of the present invention.

1 liquid-permeable surface material (nonwoven fabric)
2 liquid-impermeable leakage preventing material (water-proof sheet)
3 paper or unwoven fabric
4 liquid absorbent composite
5 pulverized pulp or cellulose powder
6 mount
7 crepe paper
8 rayon staple fiber
9 movable model of woman's waist
10 dropping tube
11 test sample
12 top opening of a burette
13 sample mount
14 air hole
15 glass filter The above mentioned liquid absorbent composite according to the present invention in itself is not satisfactory absorber, and an intended function can be exhibited only when it is used in combination with a cotton-like or sheet material.

Specifically, only when the liquid absorbent composite is incorporated into a capillary structure comprised of a fiber assembly, it can have a combination of a liquid holding space, liquid diffusing properties and shape retentivity which the fiber assembly possesses.

The material which is used in combination with the liquid absorbent composite is preferably those having a capability of absorbing, diffusing and holding a liquid. Specific examples of the material include hydrophilic cellulosic fibers such as pulp, rayon and cotton, and further a polyester subjected to a hydrophilic treatment, vinylon and an acrylic fiber having a number of micropores on the surface of the fiber.

Since these fibers are highly hydrophilic, they have a capability of rapidly diffusing a liquid into the inside of a fiber assembly and, at the same time, can surely hold the liquid through a strong capillary action.

In other words, these fibers serve to effectively transfer a liquid to the liquid absorbent composite through absorption and diffusion of the liquid and to hold the liquid until the composite completely absorbs the liquid.

Further, besides the above-mentioned hydrophilic cellulosic fibers, synthetic fibers having a high wet to dry tenacity ratio, such as polyethylene, polypropylene and polyester fibers, and polyethylenepolypropylene composite fibers, can be also used, and the use of these fibers serves to increase the structural stability of the absorber even during liquid absorption, which contributes to prevention of slippage and wilting of the absorber.

It is apparent that when the above-mentioned both kinds of fibers are used in combination according to need, the performance of the absorber can be further improved.

Various embodiments of the absorbent article according to the present invention will now be described with reference to a cross-sectional view as shown in FIG. 1. However, it is needless to say that the present invention is not limited to these embodiments.

FIG. 1(a) is a sheet absorber according to the present invention. The sheet absorber is prepared by a method which comprises uniformly applying a water absorbent composite 4 on a sheet of paper or a nonwoven fabric 3, superimposing another sheet of paper or nonwoven fabric 3' thereon, and spraying a small amount of water in the form of a mist or applying a steam on the paper or nonwoven fabric, and drying the resulting laminate to bond the upper and lower sheets of paper or nonwoven fabrics 3,3' to each other through the liquid absorbent composite 4 which was once wetted, thereby obtaining a sheet absorber having excellent flexibility. The liquid absorbent composite 4 is applied in an amount of preferably 10 g/m² to 300 g/m², more preferably 30 g/m² to 150 g/m².

FIG. 1(b) shows another embodiment of a sheet absorber according to the present invention. The sheet absorber is prepared by a method which comprises mixing a pulverized pulp or cellulose powder 5 with a liquid absorbent composite 4, molding the resulting mixture into a sheet, sandwiching the sheet between upper and lower sheets of paper or nonwoven fabrics 3 and sealing the ends of the paper or nonwoven fabrics by adhesion, thereby obtaining a sheet absorber having excellent flexibility.

FIG. 1(c) is a cross-sectional view of an example of the absorbent article of the present invention. The absorbent article is prepared by a method which comprises uniformly applying a liquid absorbent composite 4 on a pulverized pulp layer 5 laminated on a mount 6, laminating a pulverized pulp 5 on the composite, superimposing a mount 6 thereon, and covering the whole through covering of the lower side with a waterproof sheet 2 and covering of the upper side with a nonwoven fabric 1. A sheet of paper or a nonwoven fabric 3 may be interposed between the liquid absorbing composite 4 and the pulverized pulp layer 5. This structure is mainly suited for use in paper diapers.

FIG. 1(d) is a cross-sectional view of a further example of the absorbent article of the present invention. The absorbent article is prepared by a method which comprises uniformly applying a liquid absorbent composite 4 on a pulverized pulp 5 laminated on a mount 6, laminating one to ten sheets, preferably three to six sheets of crepe paper 7 thereon, laminating a waterproof sheet 2 on the side of the crepe paper 7, laminating a rayon staple fiber 8 on the side of the pulverized pulp, and covering the whole with a nonwoven fabric 1. This structure is mainly suited for use in sanitary napkins.

The absorbent article of the present invention comprises a liquid absorbent composite composed of a water absorbent polymer (A), a water-insoluble inorganic material (B), and a water-insoluble hydrophilic fibrous material (C), and exhibits excellent absorbency and retentivity with respect to high-viscosity liquids including blood, pus, and a loose passage which were absorbed and retained with difficulty in the prior art, which enables a remarkable reduction in tackiness on the surface of the article and leakage from the side which are mainly caused by the failure of absorption and retention of these liquids.

EXAMPLES OF THE INVENTION

The invention will be further illustrated below with reference to examples thereof. It is not restricted to them. It is also directed to an absorbent articles having excellent absorbency with respect to high-viscosity liquids-. Since, however, these absorbent articles can be basically treated under the same concepts, an example with respect to a sanitary napkin will now be described in more detail as a typical example of the absorbent articles.

The capacity of saturation absorption, rate of absorption and absorbing power of a liquid absorbent composite, and the amount of returned liquid and maximum dynamic absorption which are measures of the effect of the present invention were determined by the following methods.

Physiological saline was used as a typical example of the low-viscosity fluids, and blood as a typical example of the high-viscosity fluids.

(1) Capacity of saturation absorption:

A dried liquid absorbent composite was immersed in a sufficient amount of equine blood (defibrinated blood; a product sold by Nippon Bio-Supp. Center) or physiological saline and allowed to stand in that state for 30 min. Thereafter, it was filtered by suction (a filter paper No. 2; a diameter of 125 mm), followed by determination of the weight. The same procedures as that mentioned above were repeated with respect to a system free from the liquid absorbent composite (i.e., with respect to only a filter paper) to determine the weight. The capacity of saturation absorption of the liquid absorbent composite was determined from the data thus obtained by the following equation:

$$\text{capacity of saturation absorption (g/g)} = \frac{W_1 - W_0}{W}$$

wherein

W: the weight (g) of the water absorbent polymer (A) in the liquid absorbent composite;

$W_1$: the total weight (g) of the liquid absorbent composite and the filter paper after the liquid absorption; and $W_0$: the weight (g) of the filter paper after liquid absorption.

(2-1) Rate of absorption (a):

The rate of absorption was determined with an apparatus as shown in FIG. 3. A top opening 12 of a burette was stopped, and a sample mount 13 and an air hole 14 were located on the same level. 0.3 g of the liquid absorbent composite 4 was placed on a glass filter (No. 1) 15 having a diameter of 10 mm and provided in the sample mount. The amount of the defibrinated equine blood absorbed for a period of 20 min after the composite had been placed on the filter was expressed as the rate of absorption (a).

(2-2) Rate of absorption (b):

The same procedures as those described with respect to the rate of absorption (a) in the above item (2-1) were repeated to determine the amount of physiological saline which the liquid absorbent composite containing 0.3 g of a water absorbent polymer (A) immobilized thereon absorbed for a period of 1 min. The value thus obtained was expressed as the rate of absorption (b).

(3) Absorbing power:

0.5 cc of defibrinated equine blood or physiological saline was dropped on 0.05 g of a liquid absorbent composite with a dropper. The state of absorption was visually observed and evaluated according to the following four grades:

⊙ the liquid was immediately absorbed.

○ the liquid was absorbed after 2 to 3 sec.

Δ the liquid was absorbed with gradual adaptation.

X the presence of the liquid remaining unabsorbed was observed after 1 hr.

(4) Amount of returned liquid:

10 g of pseudo-blood was injected into a test sample. A pressure of 50 g/cm$^2$ was applied thereto. The returned liquid was absorbed by filter paper. The weight of the returned liquid determined was regarded as the amount of returned liquid.

(5) Maximum dynamic absorption:

A movable model of the lower half of a woman's body was provided with a test sample. The model was then subjected to walking movement at a speed corresponding to 50 m/min while pseudo-blood was injected through a dropping tube onto the test sample, thereby determining an amount of the liquid which was absorbed until the leakage from the side of the test sample was caused.

EXAMPLE 1

A 500-ml four-necked round flask equipped with a stirrer, a reflux condenser, a dropping funnel, and a nitrogen inlet tube was charged with 230 ml of cyclohexane and 1.0 g of ethylcellulose (N-100; a product of Hercules Inc.). The temperature of the resulting mixture was elevated to 75° C. Separately, 30 g of acrylic acid was neutralized in a conical flask with an aqueous solution prepared by dissolving 13.4 g of caustic soda in 39 g of water, thereby obtaining an aqueous monomer solution having a monomer concentration of 45% by weight (water content: 55% by weight). 50 mg of potassium persulfate and 65.5 mg of polyoxyethylene glycol diacrylate having 12 oxyethylene units on the average were then added to the monomer solution and homogeneously dissolved therein. The monomer solution was dropped in the above-mentioned four-necked flask in a nitrogen atmosphere for 1.5 hr, thereby causing polymerization. The contents of the flask were kept at 70° to 75° C. for 0.5 hr to complete the polymerization.

The polymerization product was separated by filtration and then dried at 80° C. in vacuo to obtain a water absorbent polymer (A-1).

20 g of the water absorbent polymer (A-1), 100 g of ion-exchanged water, 10 g of bentonite, and 10 g of cellulose powder (CF11; a product of Whatman Inc.; a fiber length of 500 μm) were kneaded for about 10 min with a twin kneader-mixer. The resulting product was dried at 80° C. in vacuo to obtain a liquid absorbent composite.

The observation of the liquid absorbent composite under an electron microscope revealed that the bentonite and cellulose powder were immobilized on the surface of the water absorbent polymer (A-1). The composite had a bulk specific gravity of 0.24 g/cc.

EXAMPLE 2

A 500-ml four-necked round flask equipped with a stirrer, a reflux condenser, a dropping funnel, and a nitrogen inlet tube was charged with 230 ml of cyclohexane and 1.0 g of ethylcellulose (N-100; a product of Hercules Inc.). The temperature of the resulting mixture was elevated to 75° C. Separately, 30 g of acrylic acid was neutralized in a conical flask with an aqueous solution prepared by dissolving 13.4 g of caustic soda in 39 g of water, thereby obtaining an aqueous monomer solution having a monomer concentration of 45% by weight (water content: 55% by weight). 50 mg of potassium persulfate was then added to the monomer solution and homogeneously dissolved therein. The monomer solution was dropped in the above-mentioned four-necked flask in a nitrogen atmosphere for 1.5 hr, thereby causing polymerization. The contents of the flask were kept at 70° to 75° C. for 0.5 hr to complete the polymerization.

Thereafter, the resulting polymerization product was subjected to azeotropic dehydration (while refluxing cyclohexane), thereby adjusting the water content of the polymer dispersed in cyclohexane to 35% by weight.

Then, an aqueous solution prepared by dissolving 0.03 g of tetraglycerol tetraglycidyl ether (a trade name: DENACOL EX-512; a product of Nagase & Co., Ltd.) in 1 ml of water was added at 73° C. The resulting mixture was kept at that temperature for 2 hr, followed by removal of cyclohexane. The polymer thus obtained was dried at 80° C. in vacuo to obtain a water absorbent polymer (A-2).

The same procedures as in Example 1 were repeated using 20 g of a water absorbent polymer (A-2), 200 g of ion-exchanged water, 10 g of bentonite, and 10 g of cellulose powder, thereby obtaining a liquid absorbent composite comprising a water absorbent polymer (A-2) and bentonite and cellulose powder each immobilized thereon and having a bulk specific gravity of 0.27 g/cc.

EXAMPLE 3

The same procedures as in Example 1 were repeated, except that, in order to change the composition of the liquid absorbent composite, 10 g of alumina was used instead of bentonite and the amount of the ion-exchanged water was 60 g, thereby obtaining a liquid absorbent composite comprising a water absorbent polymer (A-1) and alumina and cellulose powder each immobilized thereon and having a bulk specific gravity of 0.21 g/cc.

EXAMPLE 4

The same procedures as in Example 1 were repeated, except that, in order to change the composition of the liquid absorbent composite, 20 g of a pulp (fiber length: 5 mm) was used instead of cellulose powder and the amount of the water absorbent polymer (A-1) was 10 g, thereby obtaining a liquid absorbent composite comprising a water absorbent polymer (A-1) and bentonite and a pulp each immobilized thereon and having a bulk specific gravity of 0.26 g/cc.

EXAMPLE 5

A water-insoluble water absorbent polymer (A-3) in the form of white powder was prepared from corn starch, acrylic acid, acrylamide, and ethylene glycol dimethacrylate according to the method as described in Example 4 of Japanese Patent Laid-Open No. 62463/1986.

The same procedures as in Example 1 were repeated using the water absorbent polymer (A-3) thus obtained, thereby obtaining a liquid absorbent composite comprising a water absorbent polymer (A-3) and bentonite and cellulose powder each immobilized thereon and having a bulk specific gravity of 0.22 g/cc.

EXAMPLE 6

2 g of bentonite and 100 g of water were mixed with each other in a screw rotary vane mixer. 20 g of a water absorbent polymer (A-1) as used in Example 1 and 2 g of cellulose powder were successively added to the resulting mixture, followed by kneading for 5 min. The resulting product was dried at 80° C. in vacuo to obtain a liquid absorbent composite comprising a water absorbent polymer (A-1) and bentonite and cellulose powder each immobilized thereon and having a bulk specific gravity of 0.52 g/cc and a water content of 11 percent.

EXAMPLE 7

The same procedures as in Example 1 were repeated, except that, in order to change the composition of the liquid absorbent composite, the amounts of bentonite and cellulose powder were each 200 g, thereby obtaining a liquid absorbent composite comprising a water absorbent polymer (A-1) and bentonite and cellulose powder each immobilized thereon and having a bulk specific gravity of 0.08 g/cc.

COMPARATIVE EXAMPLE 1

A water absorbent polymer (A-1) as prepared in Example 1 was used as Comparative Example 1.

COMPARATIVE EXAMPLE 2

The same procedures as in Example 1 were repeated, except that no cellulose powder was used, thereby obtaining a liquid absorbent composite comprising a water absorbent polymer (A-1) and bentonite immobilized thereon and having a bulk specific gravity of 0.81 g/cc.

COMPARATIVE EXAMPLE 3

The same procedures as in Example 1 were repeated, except that no bentonite was used, thereby obtaining a liquid absorbent composite comprising a water absorbent polymer (A-1) and cellulose powder immobilized thereon and having a bulk specific gravity of 0.31 g/cc.

The capacity of saturation absorption, rate of absorption, and absorbing power were evaluated with respect to each of the liquid absorbent composites obtained in Examples 1 to 7 and Comparative Examples 1 to 3.

The results are shown in Tables 1 and 2.

TABLE 1

| | Evaluation | | |
| --- | --- | --- | --- |
| | saturation absorption (g/g) equine blood | rate of absorption (a) (cc/0.3 g) equine blood | absorbing power equine blood |
| Ex. 1 | 31.2 | 2.8 | ⊙ |
| Ex. 2 | 24 | 2.3 | ⊙ |
| Ex. 3 | 30.1 | 3.1 | ⊙ |
| Ex. 4 | 19 | 2.9 | ⊙ |
| Ex. 5 | 22 | 2.5 | ⊙ |
| Ex. 6 | 18 | 2.2 | ○ |
| Ex. 7 | — | 2.4 | ○~⊙ |
| Comp. Ex. 1 | 6 | 1.2 | Δ |
| Comp. Ex. 2 | 12 | 1.9 | Δ |
| Comp. Ex. 3 | 15 | 1.6 | ⊙ |

TABLE 2

| | Evaluation | | |
| --- | --- | --- | --- |
| | saturation absorption (g/g) physiol. saline | rate of absorption (b) (cc/0.3 g) physiol. saline | absorbing power physiol. saline |
| Ex. 1 | 60 | 6.8 | ⊙ |
| Ex. 2 | 54 | 7.4 | ⊙ |
| Ex. 3 | 56 | 6.0 | ⊙ |
| Ex. 4 | 50 | 6.8 | ⊙ |
| Ex. 5 | 52 | 6.3 | ⊙ |
| Ex. 6 | 57 | 5.8 | ⊙ |
| Comp. Ex. 1 | 58 | 3.4 | ○ |
| Comp. Ex. 2 | 57 | 4.1 | ○ |

As can be seen from Tables 1 and 2, the liquid absorbent composites of the present invention exhibited absorbency with respect to both the low-viscosity liquid and the high-viscosity liquid superior to those attained by the comparative examples. Particularly, they exhibited unprecedentedly excellent capacity of saturation absorption, rate of absorption and absorbing power with respect to the high-viscosity liquid.

EXAMPLE 8

20 g of the polymer (A-2) obtained in Example 2, 200 g of ion-exchanged water and 5 g of kaolin were successively fed into a twin kneader-mixer while stirring and kneaded therein for 5 min, followed by addition of 5 g of kaolin and 10 g of cellulose powder. The resulting mixture was kneaded for 15 min and then dried at 80° C. in vacuo to obtain a liquid absorbent composite comprising a water absorbent polymer (A-2) and kaolin and cellulose powder each immobilized thereon. The composite had a bulk specific gravity of 0.28 g/cc and a water content of 14% by weight.

EXAMPLE 9

The same procedures as in Example 1 were repeated, except that 10 g of alumina was used instead of bentonite, that the amount of the ion-exchanged water was not 100 g but 20 g, and that the ion-exchanged water was added not in the form of a liquid but by spraying. Thus, there was obtained a liquid absorbent composite comprising a water absorbent polymer (A-1) and alumina and cellulose powder each immobilized thereon and having a bulk specific gravity of 0.22 g/cc. The water content of the liquid absorbent composite was 8% by weight.

EXAMPLE 10

10 g of a water absorbent polymer (A-1) was added to 500 g of cyclohexane. 100 g of ion-exchanged water was dropped into the resulting mixture while stirring. Then, 10 g of kaolin and 10 g of a pulp (fiber length: 5 mm) were added thereto, followed by stirring for about 1 hr. The resulting product was separated by filtration and dried to obtain a liquid absorbent composite comprising a water absorbent polymer (A-1) and kaolin and a pulp each immobilized thereon. The composite had a bulk specific gravity of 0.16 g/cc and a water content of 13% by weight.

EXAMPLE 11

10 g of the polymer (A-3) obtained in Example 5, 200 g of ion-exchanged water, 100 g of talc and 100 g of cellulose powder were successively fed into a twin-cylinder blender of a rotary container type. The blender was rotated for about 1 hr, and the resulting blend was dried at 80° C. in vacuo, thereby obtaining a liquid absorbent composite comprising a water absorbent polymer (A-3) and talc and cellulose powder each immobilized thereon and having a bulk specific gravity of 0.25 g/cc. The liquid absorbent composite has a water content of 16% by weight.

EXAMPLE 12

The same procedures as in Example 1 were repeated, except that the twin kneader-mixer was heated at 80° C. and that the kneading was conducted with the kneader-mixer closed tightly. Thus, there was obtained a liquid absorbent composite comprising a water absorbent polymer (A-1) and bentonite and cellulose powder each immobilized thereon and having a bulk specific gravity of 0.22 g/cc. The liquid absorbent composite had a water content of 9% by weight.

COMPARATIVE EXAMPLE 4

A water absorbent polymer (A-1), bentonite, and cellulose powder were mixed with each other in the same manner as in Example 1, except that no ion-exchanged water was added. The observation of the resulting mixture under an electron microscope revealed that bentonite and cellulose powder were not immobilized on the water absorbent polymer (A-1). The mixture had a bulk specific gravity of 0.25/cc.

COMPARATIVE EXAMPLE 5

The same procedures as in Example 1 were repeated, except that the amount of the ion-exchanged water was 800 g. However, the mixture became pasty in the step of kneading, which not only made it difficult to conduct kneading but also required a long time in subsequent steps of drying and pulverization. The resulting composite had a bulk specific gravity of 0.31 g/cc and a water content of 18% by weight. The observation of the composite under an electron microscope revealed that most of the bentonite and cellulose powder was included within the composite.

The capacity of saturation absorption, rate of absorption, and absorbing power were evaluated with respect to each of the liquid absorbent composites obtained in Examples 8 to 12 and Comparative Examples 4 and 5. Results are shown in Tables 3 and 4.

TABLE 3

| | Evaluation | | |
|---|---|---|---|
| | saturation absorption (g/g) equine blood | rate of absorption (a) (cc/0.3 g) equine blood | absorbing power equine blood |
| Ex. 8 | 28.5 | 3.5 | ⊚ |
| Ex. 9 | 27.4 | 3.0 | ⊚ |
| Ex. 10 | 29.2 | 2.5 | ○ |
| Ex. 11 | 26.3 | 3.4 | ○–⊚ |
| Ex. 12 | 27.1 | 3.4 | ⊚ |
| Comp. Ex. 4 | 11.8 | 1.5 | ○ |
| Comp. Ex. 5 | 14.2 | 1.8 | △ |

TABLE 4

| | Evaluation | | |
|---|---|---|---|
| | saturation absorption (g/g) physiol. saline | rate of absorption (b) (cc/0.3 g) physiol. saline | absorbing power physiol. saline |
| Ex. 8 | 58 | 7.9 | ⊚ |
| Ex. 9 | 59 | 7.5 | ⊚ |
| Ex. 10 | 57 | 6.6 | ⊚ |
| Ex. 11 | 53 | 7.7 | ⊚ |
| Ex. 12 | 56 | 7.8 | ⊚ |
| Comp. Ex. 4 | 57 | 4.1 | ○–⊚ |
| Comp. Ex. 5 | 59 | 5.0 | ○–⊚ |

It is noted from the data of Tables 3 and 4 that the composites obtained by the new process of the invention exhibited an excellent absorbency with respect to both the low-viscosity liquid and the high-viscosity liquid. Particularly, they were remarkably superior in capacity of saturation absorption, rate of absorption and absorbing power with respect to the high-viscosity liquid to those of the products obtained in the comparative examples.

EXAMPLE 13

20 g of polysodium acrylate as the water absorbent polymer (A), 100 g of ion-exchanged water, 10 g of bentonite as the water-insoluble inorganic material (B), and 10 g of cellulose powder (CF11; a product of Whatman Inc.; a fiber length of about 500 μm) as the water-insoluble hydrophilic fibrous material (C) were kneaded with each other for about 10 min by means of a twin kneader. The resulting product was dried at 80° C. in vacuo to obtain a liquid absorbent composite. The observation of the composite under an electron microscope revealed that the bentonite and cellulose powder were immobilized on the surface of the water absorbent polymer. The composite had a bulk specific gravity of 0.24 g/cc.

Liquid absorbent composites were prepared in the same manner as that mentioned above, except that the water absorbent polymer (A), the water-insoluble inorganic material (B), and the water-insoluble hydrophilic fibrous material (C) were varied as shown in Table 5.

The absorbency of the liquid absorbent composites thus obtained is shown in Table 5. For comparison, the absorbency of a comparative sample consisting of only the water absorbent polymer (A), a comparative sample consisting of only the water absorbent polymer (A) and the water-insoluble inorganic material (B), and a comparative sample consisting of only the water absorbent polymer (A) and the water-insoluble hydrophilic fibrous material (C) is also shown in Table 5.

Sanitary napkins having a structure as shown in FIG. 1(d) were prepared from the liquid absorbent composites and comparative samples thus obtained.

In the preparation of the sanitary napkins, the absorbing layer was formed from 0.6 g of a liquid absorbent composite, 2.0 g of flocculent pulp, 1.5 g of absorbent paper and 0.3 g of rayon staple fiber, while the surface sheet was formed from a heat bonded nonwoven fabric composed of 65% of a polyester fiber and 35% of a polyethylene/polypropylene composite fiber and having an a real weight of 20 g/m$^2$. Further, a laminate composed of waterproof paper (25 g/m$^2$) and 10 μm-thick polyethylene laminated thereon was used as the waterproof sheet.

The amount of returned liquid and maximum dynamic absorption were determined with respect to each sanitary napkin thus obtained. The results are shown in Table 5.

As can be seen from Table 5, the absorbent articles of the present invention exhibit excellent absorbency with respect to high-viscosity liquids such as blood.

TABLE 5

| sample | water absorbent polymer (A) | water-insoluble inorganic material (B) | water-insoluble hydrophilic fibrous material (C) | blending weight ratio (A/B/C) | saturation absorption (g/g) equine blood | saturation absorption (g/g) physiol. saline | rate of absorption (cc/0.3 g) equine blood | rate of absorption (cc/0.3 g) physiol. saline | absorbing power equine blood | absorbing power physiol. saline | bulk specific gravity (g/cc) | amount of returned liquid (g) | maximum dynamic absorption (g) |
|---|---|---|---|---|---|---|---|---|---|---|---|---|---|
| liquid absorbent composite (1) | polysodium acrylate | bentonite | cellulose powder | 2/1/1 | 31.2 | 60 | 2.8 | 6.8 | ⊙ | ⊙ | 0.24 | 1.1 | 8.5 |
| liquid absorbent composite (2) | polysodium acrylate | alumina | cellulose powder | 2/1/1 | 30.1 | 56 | 3.1 | 6.0 | ⊙ | ⊙ | 0.21 | 1.0 | 9.2 |
| liquid absorbent composite (3) | polysodium acrylate | bentonite | flocculent pulp | 1/1/2 | 19 | 50 | 2.9 | 6.8 | ⊙ | ⊙ | 0.26 | 1.3 | 7.5 |
| liquid absorbent composite (4) | polysodium acrylate | " | cellulose powder | 10/1/1 | 18 | 52 | 2.2 | 5.8 | ○ | ⊙ | 0.52 | 1.4 | 7.4 |
| liquid absorbent composite (5) | polysodium acrylate | " | cellulose powder | 1/10/10 | — | — | 2.4 | — | ⊙ | ⊙ | 0.08 | 1.6 | 6.8 |
| liquid absorbent composite (6) | starch-acrylic acid graft copolymer | " | cellulose powder | 2/1/1 | 22 | 52 | 2.5 | 6.3 | ⊙ | ⊙ | 0.22 | 1.7 | 6.5 |
| comparative sample (1) | polysodium acrylate | — | — | — | 8 | 58 | 1.2 | 3.4 | △ | ○ | 0.95 | 2.3 | 4.9 |
| comparative sample (2) | polysodium acrylate | bentonite | — | 2/1/0 | 12 | 57 | 1.9 | 5.0 | △ | ○ | 0.81 | 2.2 | 5.0 |
| comparative sample (3) | polysodium acrylate | — | cellulose powder | 2/0/1 | 15 | — | 1.8 | — | ⊙ | ⊙ | 0.31 | 2.5 | 4.8 |

What is claimed is:

1. A liquid absorbent composite which comprises:
   (a) granules of a water-absorbent polymer;
   (b) a water-insoluble inorganic material; and
   (c) water-insoluble hydrophilic fibers having a length of 50 mm or less and wherein (b) and (c) are embedded in or deposited on the surface of said granules; and wherein the weight ratio between (a) to (b) to (c) is 100:5–1200:5–1200, respectively.

2. The liquid absorbent composite as claimed in claim 1, which has a bulk specific gravity of 0.03 to 0.7 g/cc.

3. The liquid absorbent composite as claimed in claim 1, wherein said water-absorbent polymer (a) is a water-soluble, ethylenically unsaturated monomer or a crosslinked product thereof, which includes acrylic acid or a salt of acrylic acid as the major component thereof.

4. The liquid absorbent composite as claimed in claim 1, wherein said inorganic material (b) is selected from the group consisting of alumina, silica, zeolite, a clay of the montmorillonite group and a clay of the kaolinite group.

5. The liquid absorbent composite as claimed in claim 1, in which said hydrophilic fiber (c) is natural or artificial cellulose.

6. An absorbent article which comprises said absorbent composite as defined in claim 1.

7. The liquid-absorbent composite of claim 1, wherein said water-absorbent polymer is a polymer capable of absorbing water in an amount of 22 cc/g of said polymer.

8. The liquid absorbent composite of claim 1, wherein said granules have a mean particle diameter of 10 to 3000 μm.

* * * * *